United States Patent [19]
Reed, Jr.

[11] Patent Number: 5,827,530
[45] Date of Patent: Oct. 27, 1998

[54] FILLABLE PATCH FOR DERMAL OR TRANSDERMAL DELIVERY

[76] Inventor: Fred Dewitt Reed, Jr., 62 Macon Ave., Asheville, N.C. 28801

[21] Appl. No.: 782,313

[22] Filed: Jan. 15, 1997

Related U.S. Application Data

[63] Continuation-in-part of Ser. No. 596,572, Feb. 5, 1996.
[51] Int. Cl.[6] .................................................. A61F 13/00
[52] U.S. Cl. ........................ 424/449; 424/447; 424/448; 604/41
[58] Field of Search .................................. 424/447, 448, 424/449; 604/41

[56] References Cited

U.S. PATENT DOCUMENTS

| | | | |
|---|---|---|---|
| 4,340,048 | 7/1982 | Eckenhoff | 128/213 R |
| 4,460,368 | 7/1984 | Allison | 604/896 |
| 4,552,561 | 11/1985 | Eckenhoff | 604/896 |
| 4,605,399 | 8/1986 | Weston | 604/305 |
| 5,286,258 | 2/1994 | Haber | 604/90 |
| 5,441,490 | 8/1995 | Svedman | 604/289 |
| 5,614,212 | 3/1997 | D'Angelo | 424/449 |

*Primary Examiner*—D. Gabrielle Brouillette

[57] ABSTRACT

A fillable dermal or transdermal delivery device that utilizes injection ports for post assembly introduction of medicinally active or inactive agents. The device is comprised of a pressure sensitive skin contact adhesive layer which is affixed to a diffusion membrane comprised of a porous film. A backing layer is provided and is sealed along its perimeter to the perimeter of the porous film, thereby creating a fillable reservoir. The reservoir is filled by means of a loading port that is comprised of a septum. The fillable reservoir is filled by means of a loading needle such as a hypodermic needle that is inserted through the septum of the loading port. A shield is provided in the interior of the fillable reservoir to protect the diffusion membrane from damage in the event that the hypodermic needle is inserted far enough through the loading port to make contact with the porous film.

28 Claims, 5 Drawing Sheets

FILLABLE PATCH FOR DERMAL OR TRANSDERMAL DELIVERY

CROSS-REFERENCE TO RELATED APPLICATION

The instant application is a continuation-in-part of applicant's copending application, Ser. No. 08/596,572, entitled *Fillable Patch for Dermal or Transdermal Delivery*, filed Feb. 5, 1996.

BACKGROUND OF THE INVENTION

1. Field of the Invention

The present invention relates generally to medication application systems and more particularly relates to a device, which is fillable after assembly, that releases medicinally active or inactive agents either to or through the skin.

2. Prior Art

Traditionally, drugs and medication have been administered either orally or by injection. These methods have certain well-known disadvantages that are pointed out in the prior art, primarily the risk of infection with respect to administering medication by injection, and the need to disperse the agent throughout the circulatory system for oral administration. To avoid the problems of oral or injection methods of application, it is well-known in the art to administer agents through a porous film to and through the skin of the patient. This type of application system is sometimes referred to as a "dermal or transdermal delivery system."

An example of a transdermal skin patch for the application of medication is found in U.S. Pat. No. 4,201,211 to Chanderasekaran. The Chanderasekaran patent describes a skin patch for delivering medication to the patient's skin. The medication is absorbed at a controlled rate that depends principally on the concentration of the medication and the porosity of the micro-porous membrane that is in contact with the skin. Another similar device is taught in U.S. Pat. No. 3,996,934 and 3,742,951 to Zaffaroni. Both of these patents disclose "bandage type" applications. In "bandage type" applications the medication is dispersed in a carrier layer that alone or with a metering layer of micro-porous film establishes a medication flow rate to the skin. Because of the need for dispersion, it is necessary that the medication must be non-reactive with the carrier layer material and therefore requires specific materials for the construction of the reservoir layer depending on the medication.

This requirement of specific materials for use with different agents has typically resulted in the manufacture of delivery devices with medication in place. A result has been problems with diminished shelf life of the delivery device since the medication is subject to deterioration when it is loaded or manufactured into the delivery device. Additionally, medications exist for which it is impossible to find a compatible dispersing material possessing a lengthy shelf life. Furthermore, the complete package is inherently fragile due to the fragile nature of the reservoir layer.

In other "bandage type" applicators, the medication material is carried as a gelatinous material in a reservoir. Problems with these systems include difficulties in loading the delivery device and lateral medication leakage during use. A result of medication leakage may be the undesirable staining of clothing or skin.

U.S. Pat. No. 4,460,368 to Allison et al. teaches a transdermal delivery system that is fillable with a variety of medications and is capable of being filled by the prescriber or pharmacist supplier of the patient. One embodiment of the Allison device teaches insertion of a needle filling tool, which penetrates and loads the device by injecting medication into the device. The filling tool is then withdrawn after filling. A potential problem with Allison device is the membrane of the device can be damages by the insertion of the filling tool. Damage could occur, for example, if the practitioner administering the agent inserts the tool too far into the interior of the device and makes contact with the opposite wall.

In addition to dermal or transdermal delivery of medication, there exists a growing interest in the dermal or transdermal delivery of agents for aromatheraphy, herbal therapy, local anesthesia and analgesia since, with dermal or transdermal delivery, the skin is not broken. As a result, the risk of infection is low. Another advantage is the pain free delivery of agents to a patient. These factors are partially responsible for the growing popularity of dermal or transdermal delivery systems.

Consequently, a post manufacture fillable dermal or transdermal delivery device is desired that does not possess the disadvantages of the prior art.

SUMMARY OF THE INVENTION

It is therefore an object of the invention to provide a dermal or transdermal delivery device that is capable of being filled after assembly of the device. A further object of the invention is to provide a delivery device which is capable of being filled without the risk of damage to the diffusion membrane, which is comprised of micro-porous or macro-porous films to which the contact adhesive is applied.

More particularly, the preferred embodiment of the invention is a fillable dermal or transdermal device that comprises a pressure sensitive skin adhesive layer for making contact with the patient's skin. A release liner is removably affixed to the adhesive layer to cover and protect the pressure sensitive adhesive layer until such time as it is to be used. A reservoir for containing medicinally active or inactive agents is provided in the device. One side of the reservoir is comprised of a diffusion membrane or porous film adjacent the adhesive layer. The porous film delivers the agent to the patient's skin. The other side of the reservoir is comprised of a backing layer. Preferably, the backing layer is occlusive, porous, or perforated. The backing layer may be constructed of a micro-porous layer that permits vapor to exit or pass through the backing layer. The backing layer and the porous film are fused together, preferably heat sealed about their perimeters. The heat seal may be accomplished by placing an acceptable and compatible heat seal material such as vinyl or urethane between the backing layer and porous film. The medicinally active or inactive agents are delivered into the reservoir by means of a loading needle, such as a hypodermic needle, that penetrates a self-sealing loading port, preferably a rubber septum. The rubber septum in the preferred embodiment penetrates or passes through, or is heat sealed to the reservoir side of the backing layer which itself may or may not be perforated. Alternatively, the rubber septum can be incorporated in the seal formed about the perimeter of the reservoir where the backing layer and diffusion membrane or porous film are fused together. Placed inside of the reservoir is a shield, such as a thin aluminum wafer that is positioned against but not attached to the inside surface of the diffusion membrane or porous film to provide protection to the film in the event that the hypodermic needle is inserted too far through the loading port or rubber septum. The shield prevents the hypodermic needle from making contact with and damaging the porous film.

In practice, the dermal or transdermal delivery device is provided to practitioners without medicinally active or inactive agents loaded in the device. The absence of such agents results in a greatly extended shelf life for the delivery device. When a dermal or transdermal delivery device is required, the device can then be filled and/or refilled with the appropriate agent or agents by means of a hypodermic needle inserted through the rubber septum. The filled device is then provided to a patient. The patient then removes the release liner that covers the pressure sensitive adhesive layer. The adhesive layer can then be applied to the skin of the patient. The medicinally active or inactive agents contained in the device then diffuse through the single or multiple combination of micro-porous or macro-porous films. The agents are then absorbed through or reside on the skin of the patient, depending on the physicochemicl properties of the medicinal agent.

DETAILED DESCRIPTION OF THE PREFERRED EMBODIMENTS

Figure 1:
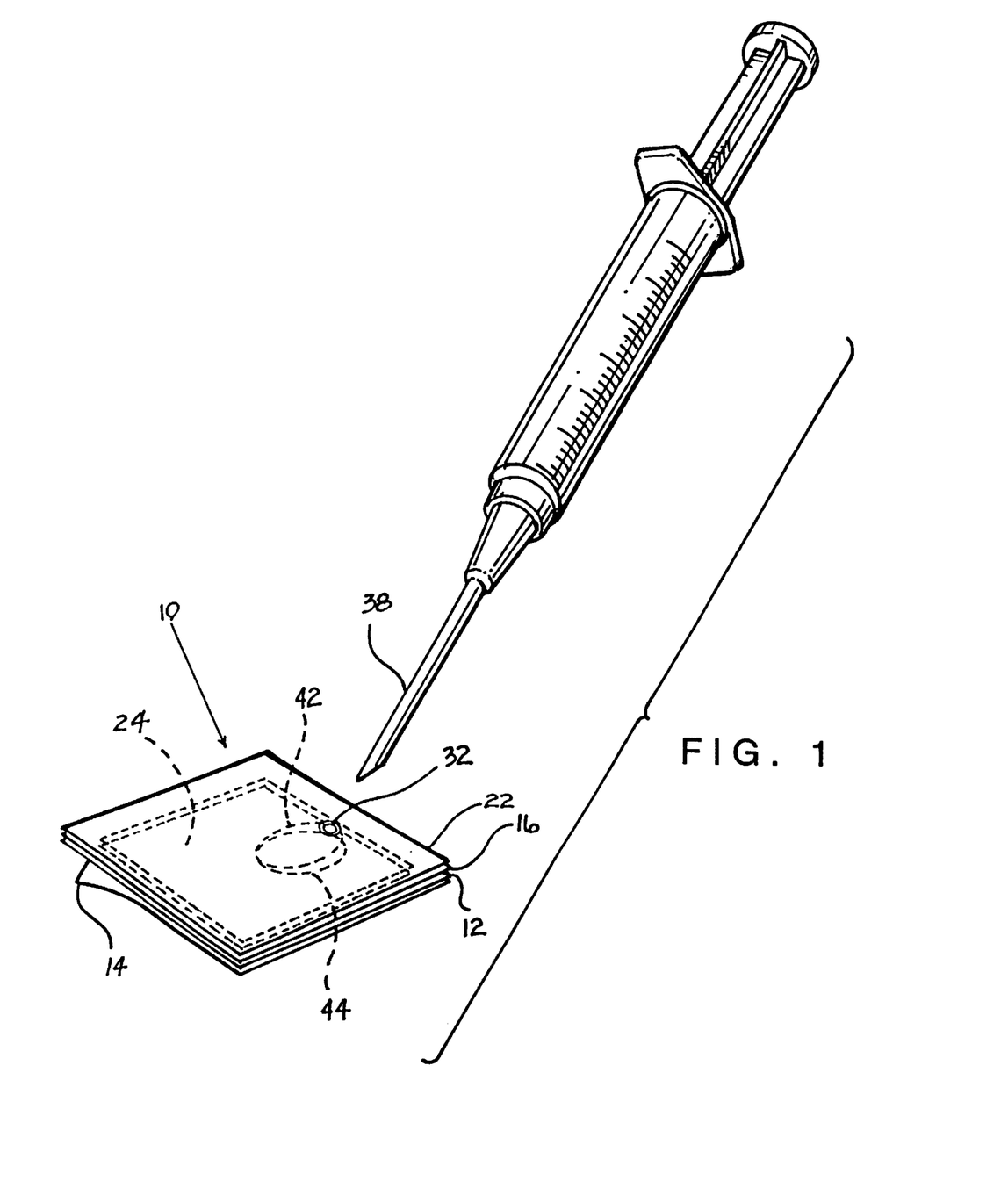
FIG. 1 is a perspective view of the dermal or transdermal delivery device and hypodermic needle.
Figure 2:
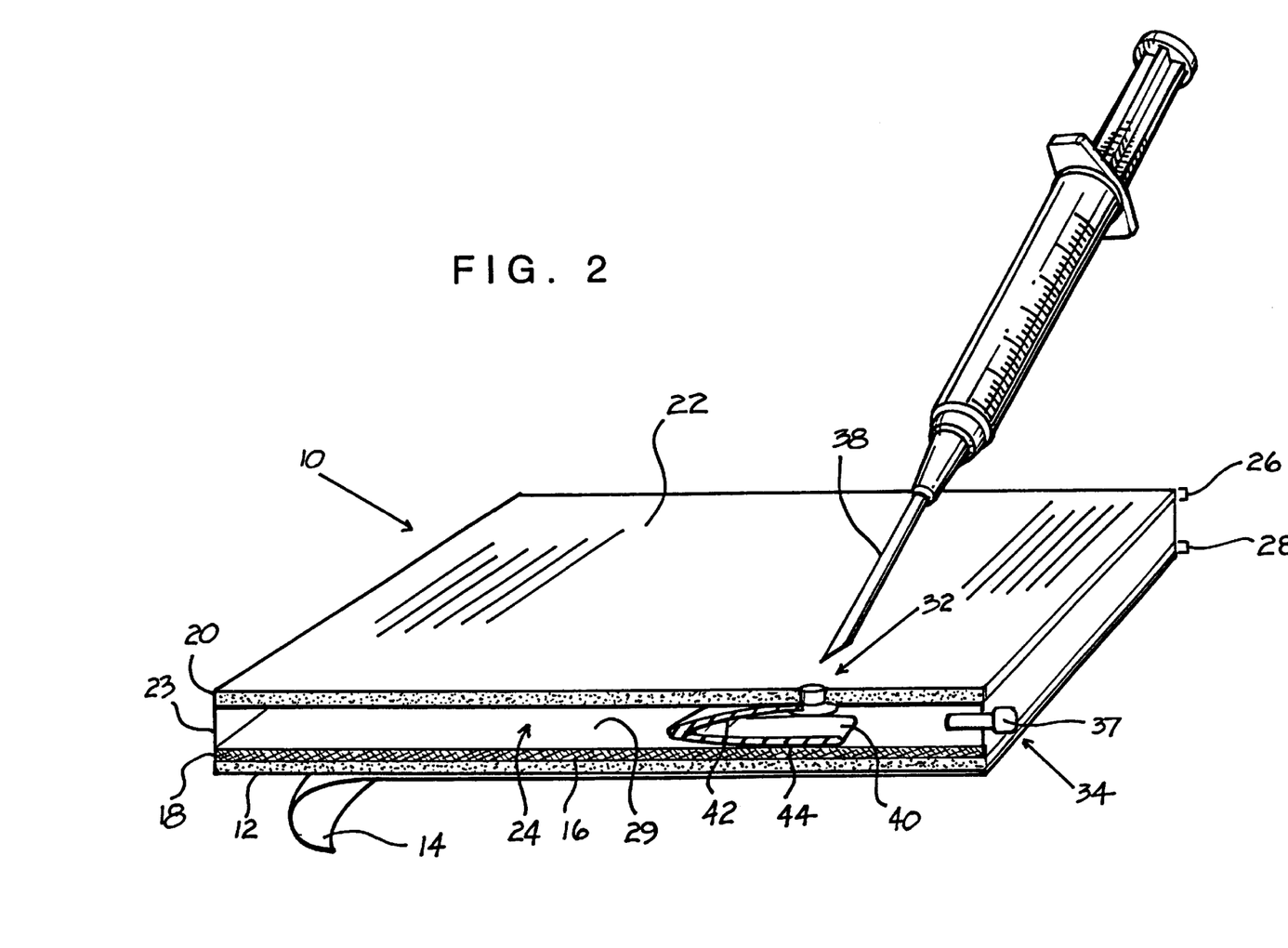
FIG. 2 is a partial cut-away view of the dermal or transdermal delivery device.

Referring to FIGS. 1 and 2, the dermal or transdermal delivery device is designated generally 10. Dermal or transdermal delivery device 10 comprises a pressure sensitive skin contact adhesive layer 12 for affixing the dermal or transdermal delivery device 10 to the skin of a patient. Release liner 14 is provided to protect skin contact adhesive layer 12 until such time as the dermal or transdermal delivery device 10 is ready for use. Release liner 14 is peelable from the skin contact adhesive layer 12 and should be removed and discarded when dermal or transdermal delivery device 10 is ready for use. Diffusion membrane 16 is affixed to skin contact adhesive layer 12 is comprised of a single or multiple combination of micro-porous or macro-porous films through which medicinally active and-or inactive agents diffuse. Perimeter 18 of diffusion membrane 16 is preferably heat sealed to perimeter 20 of backing layer 22 to form sealed edge 23. The resulting cavity formed by diffusion membrane 16 and backing layer 22 is fillable reservoir 24. Therefore, fillable reservoir 24 is defined ion one side by backing layer 22 which forms the distal or outer side 26 of the fillable reservoir 24. Fillable reservoir 24 is defined on the other side by diffusion membrane 16 which forms the proximal or skin side 28 of the fillable reservoir 24. Diffusion membrane 16, which forms one wall of tillable reservoir 24, has inside surface 29 defined thereon. Fillable reservoir 24 is provided with loading port 32 wherein rubber septum 26 is heat sealed to backing layer inside surface 21. A perforation can be made in backing layer 22 to coincide with rubber septum 36, otherwise backing layer 22 must be penetrated before rubber septum 36 can be penetrated. Rubber septum 36 prevents the agents from escaping. An alternate embodiment is to position loading port 32 to pass through backing layer 18. An additional embodiment is to position loading port 34 to pass through sealed edge 23, between heat sealed perimeter 20 of backing layer 22 and perimeter 18 of diffusion membrane 16. Preferably, loading ports 32 and 34 are comprised of rubber septum 36 or 37. In the preferred embodiment, rubber septum 36 is comprised of latex or other rubber material through which loading needle 38 can be sealably inserted for purposes of filling tillable reservoir 24. When needle 38 is withdrawn, rubber septum 36 will seal closed. To protect diffusion membrane 16, shield 40 is provided in the interior of tillable reservoir 24. Shield 40 is constructed of aluminum in the preferred embodiment although other pharmaceutically safe materials, either metallic and non-metallic, e.g. plastic or composite material, could be used. Furthermore, in the preferred embodiment, shield 40 is comprised of an upper surface 42 and a lower surface 44. Lower surface 44 is adjacent interior surface 29 of diffusion membrane 16 and is positioned directly opposite loading port 32 to prevent loading needle 38 from damaging diffusion membrane 16. Lower surface 44 is preferably flexibly attached to upper surface 42, thereby enabling fillable reservoir 24 to be compressed without damage to diffusion membrane 16 by lower surface 44. Alternatively, shield 40 may be free floating within fillable reservoir 24 of the device and of a size such that loading needle 38 is prevented from piercing diffusion membrane 16.

In practice, dermal or transdermal delivery device 10 can be stored for long periods of time since its shelf life is not dependent upon the medicinally active or inactive agents. This is because the agents are not injected into loading port 32 or 34 until dermal or transdermal delivery device 10 is ready for use. When ready for use, loading needle 38 is utilized to penetrate septum 36 and inject medicinally active or inactive agents into reservoir 24. Release liner 14 is peeled away from skin contact adhesive layer 12. Dermal or transdermal delivery device 10 is then affixed to the skin of the patient. After affixing dermal or transdermal delivery device 10 to a patient's skin, the medicinally active or inactive agents present in the fillable reservoir 24 diffuse through porous film 16 where the agents can then be absorbed by the skin. If necessary, fillable reservoir 24 can be refilled by loading needle 38 while fillable reservoir 24 is affixed to the patient. When loading needle 38 passes through septum 36 of loading port 32, shield 40 acts as a stop member which provides protection from damage to the diffusion membrane 16.

Figure 3:
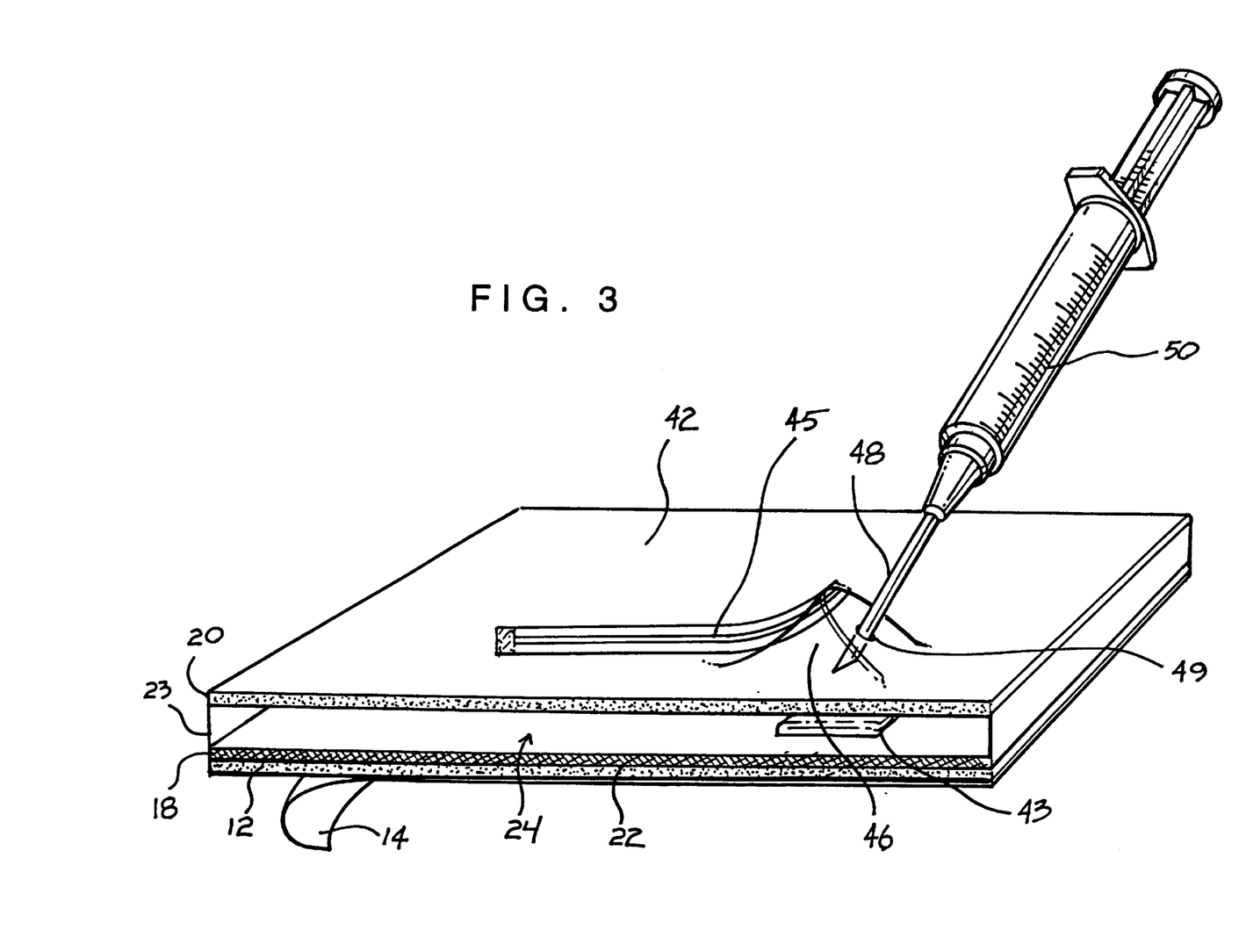
FIG. 3 is a partial cut-away view of another embodiment of a topical delivery device.

Referring to FIG. 3 backing layer 42 differs from backing layer 22 of FIGS. 1 and 2 in that layer 42 is an elastomeric material of suitable thickness such that layer 42 when pinched and stretched upward from the upper surface of the device using forceps 44 thereby forming a puckered wrinkle 46 in backing layer 42 into which needle 48 is inserted thereby piercing backing layer 42 forming a puncture hole 49 and enabling introduction of the contents of syringe 50 into reservoir 24. The free floating shield 43 in reservoir 24 prevents needle 48 from piercing layers 22, 12 and 14. Removal of the needle 48 and syringe 50 and release of the puckered wrinkle 46 from the forceps 44 allows the backing layer 42 to contract, sealing puncture hole 49 thereby preventing the contents of reservoir 24 from exiting the device through the backing layer 42.

Figure 4:
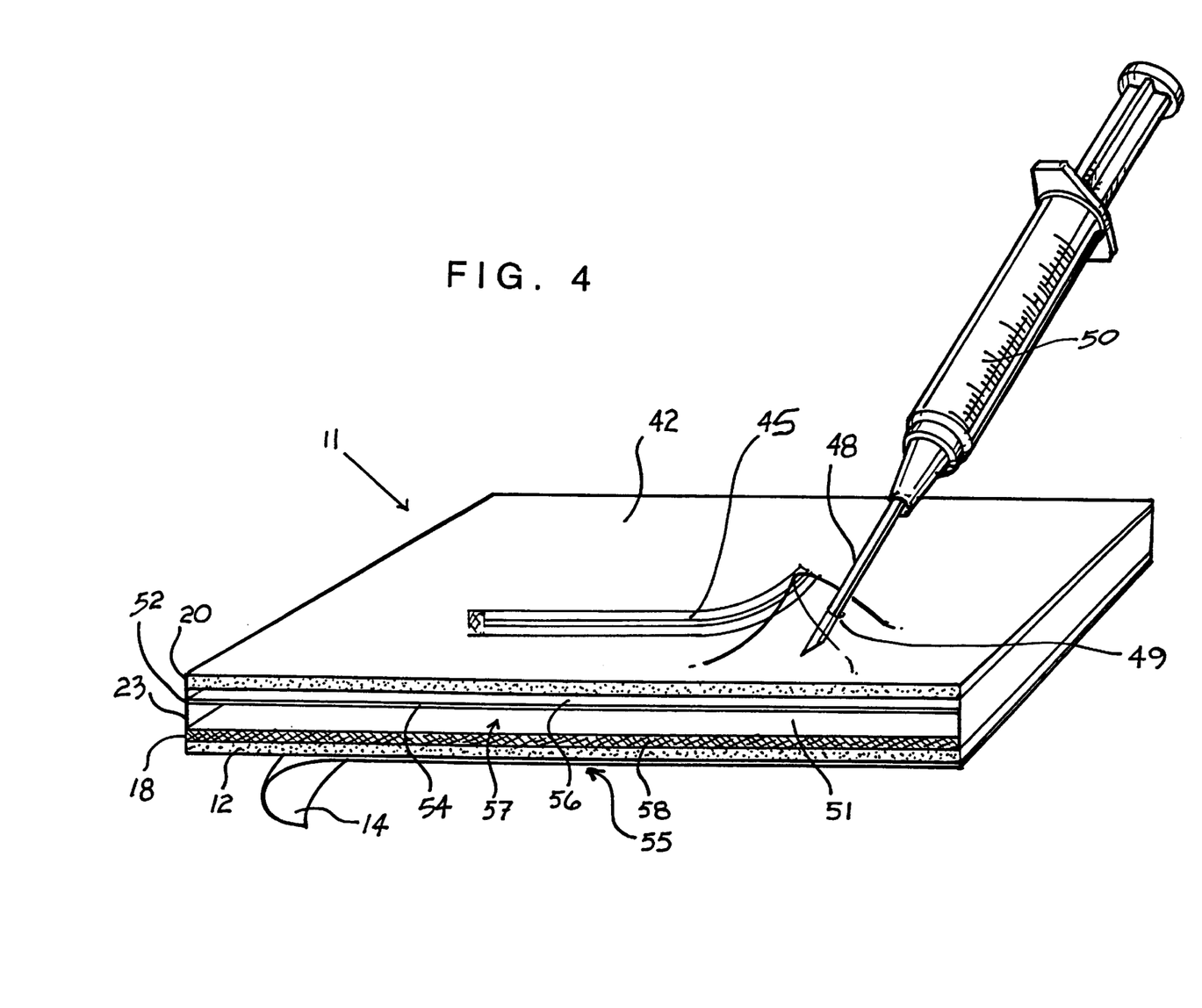
FIG. 4 is a partial cut-away view of a further embodiment of an topical delivery device.

Referring to FIG. 4, the topical delivery device is designated as 11. This device differs from device 10 in that all layers are elastomeric except that the release line 14 may also be of segmented, multi-piece construction. A two piece release liner 14 is shown in FIG. 4, indicated as a lateral slit 55 across release liner 14 thereby creating two segments. Slicing the release liner 14 of device 11 into segments allows said device to stretch laterally perpendicular to the direction of the slice as slit 55 when pulled apart laterally. Perimeter 52 of micro-pierced elastomeric membrane 54 is fused between elastomeric backing layer 42 and elastomeric diffusion layer 58 thereby dividing the reservoir 24 depicted in FIGS. 1, 2 and 3 into reservoir 56, defined by micro-pierced elastomeric layer 54 on one side and elastomeric backing layer 42 on the other side and reservoir 57, defined by the micro-pierced elastomeric layer 54 on one side and the elastomeric micro-porous or macro-porous diffusion layer 58 to which is attached the adhesive layer 12 being protected by release liner 14. As the device 11 backing layer is pierced via puckered wrinkle 46 through puncture hole 49 only reservoir 56 is filled with the contents of syringe 50 through needle 48. The contents of reservoir 56 are introduced into reservoir 57 by stretching the device 11, thereby causing openings to form at the sites of the normally closed and invisible micro-piercings 51 in elastomeric layer 54, and applying pressure to backing layer 42 thereby filling reservoir 57.

Figure 5:
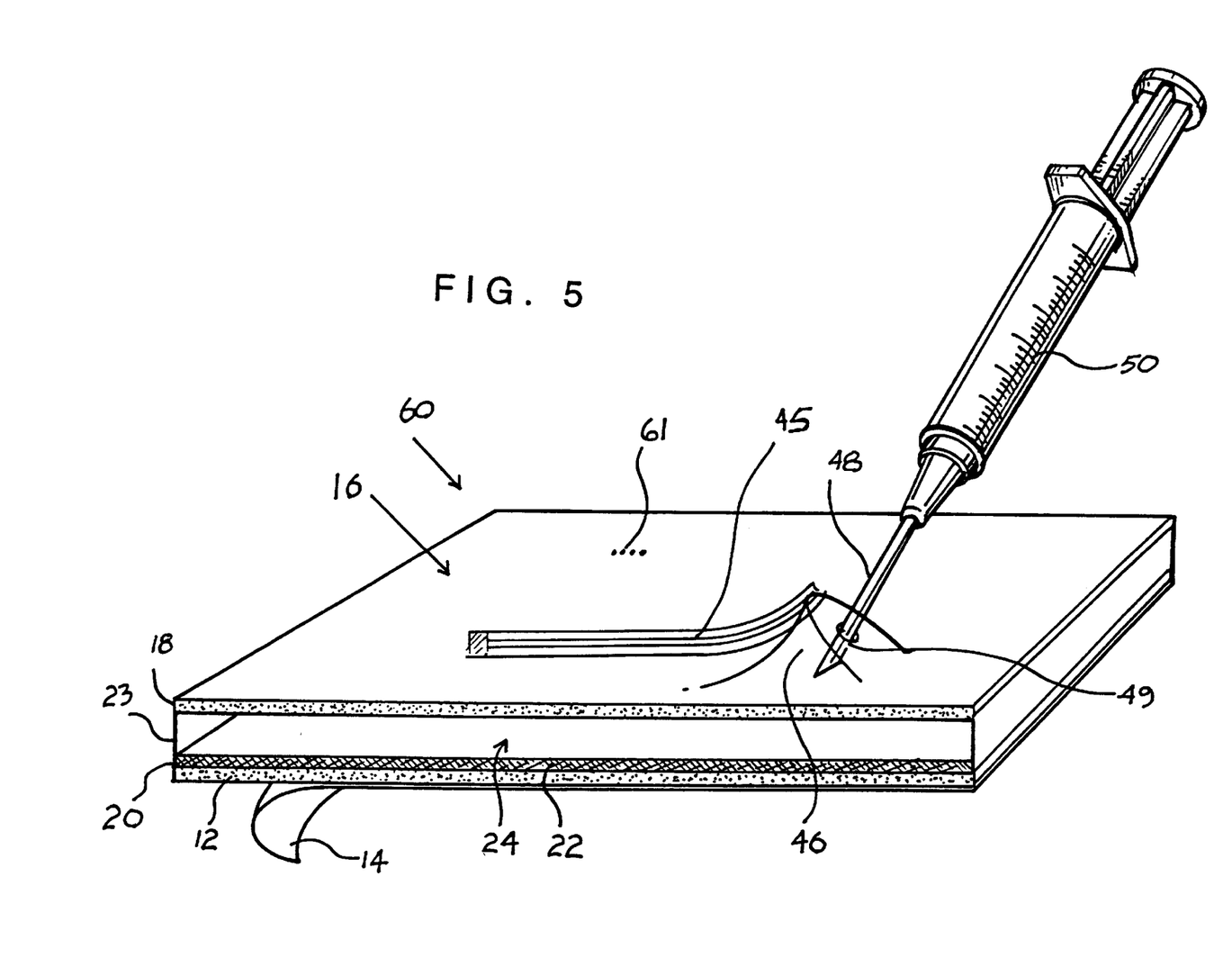
FIG. 5 is a partial cut-away view of yet another embodiment of an topical delivery device.

Referring to FIG. 5, the dermally applied device is designated generally 60. This differs from device 10 in that the positions of layers 16 and 22 are interchanged such that the pores 61 or oriented away, on the opposite side from the skin. In this configuration the device is capable of emitting vapor to the ambient environment when the reservoir 24 is filled with the appropriate agent. This device 60 is to be adhered to the septum of the nose or applied to the skin between the upper lip and the nose in such fashion that vapor from agents in the device reservoir 24 or emitted through macro-porous or micro-porous layer 16 and inhaled over an extended period of time.

Whereas, the present invention has been described in relation to the drawings attached hereto, it should be understood that other and further modifications, apart from those shown or suggested herein, may be made within the spirit and scope of this invention.

I claim:

1. A fillable agent delivery device for delivery of agents comprising:
   a fillable reservoir defined by a diffusion membrane having a perimeter and a backing layer having a perimeter, the diffusion membrane and the backing layer joined to form a seal at their respective perimeters;
   a skin contact adhesive layer carried by one of the diffusion layer and the backing layer for adhering the device to skin;
   self sealing access means for receiving a loading needle; and
   protection means for protecting the diffusion membrane from damage from the loading needle, the protection means comprising one or more of a group comprising:
   a shield positioned inside the reservoir, the shield having a surface positioned opposite the access means; and
   a puckered wrinkle releasably formed in the backing layer by pinching, the backing layer being an elastomeric material comprising the self sealing access means.

2. A fillable agent delivery device as claimed in claim 1 wherein the access means includes a self sealing port.

3. A fillable agent delivery device as claimed in claim 2 wherein the self sealing port is comprised of a rubber septum.

4. A fillable agent delivery device as claimed in claim 2 wherein the self sealing port penetrates the seal.

5. A fillable agent delivery device as claimed in claim 2 wherein the self sealing port is heat sealed around a hole formed in the backing layer.

6. A fillable agent delivery device as claimed in claim 2 wherein the self sealing port is heat sealed to the backing layer such that when filling the device the backing layer must be penetrated along with the self sealing port.

7. A fillable agent delivery device as claimed in claim 1 further including a dividing membrane positioned between the diffusion membrane and the backing membrane, the dividing membrane having a perimeter coupled to the seal, the dividing membrane dividing the reservoir.

8. A fillable dermal or transdermal device for delivery of agents to or through the skin comprising:
   a skin contact adhesive layer;
   a diffusion membrane having a perimeter and forming a proximate side of a fillable reservoir, the diffusion membrane adjacent the adhesive layer and having an interior surface;
   a backing layer having a perimeter and forming a distal side of the fillable reservoir, the backing layer forming a seal with the diffusion membrane;
   self sealing access means for receiving a loading needle; and
   a shield for protecting the diffusion membrane from damage from the loading needle, the shield positioned inside the reservoir and having a surface positioned opposite the access means.

9. A fillable dermal or transdermal device as claimed in claim 8 wherein the access means includes a self sealing port.

10. A fillable dermal or transdermal device as claimed in claim 9 wherein the self sealing port is comprised of a rubber septum.

11. A fillable dermal or transdermal device as claimed in claim 9 wherein the self sealing port penetrates the seal.

12. A fillable dermal or transdermal device as claimed in claim 9 wherein the self sealing port is heat sealed around a hole formed in the backing layer.

13. A fillable dermal or transdermal device as claimed in claim 9 wherein the self sealing port is heat sealed to the backing layer such that when filling the device the backing layer must be penetrated along with the self sealing port.

14. A fillable dermal or transdermal device as claimed in claim 8 wherein the access means includes the backing layer being formed of an elastomeric material which when penetrated, will self seal.

15. A fillable dermal or transdermal device as claimed in claim 8 wherein the backing layer is permeable to vapor such that vapor can exit or pass through the backing layer into ambient air.

16. A fillable dermal or transdermal device as claimed in claim 8 further including a dividing membrane positioned between the diffusion membrane and the backing membrane, the dividing membrane having a perimeter coupled to the seal, the dividing membrane dividing the reservoir and controlling movement of the agent from one portion of the reservoir to another.

17. A method of delivering an agent comprising the steps of:
   providing a fillable agent delivery device for delivery of agents, the device comprising:
   a fillable reservoir defined by a diffusion membrane having a perimeter and a backing layer having a perimeter, the diffusion membrane and the backing layer joined to form a seal at their respective perimeters;

a skin contact adhesive layer carried by one of the diffusion layer and the backing layer for adhering the device to skin;

self sealing access means for receiving a loading needle; and protection means for protecting the diffusion membrane from damage from the loading needle;

providing a loading needle containing an agent;

inserting the needle through the access means of the device, the diffusion membrane protected from damage from the loading needle by the protection means;

injecting the agent into the reservoir;

removing the needle; and adhering the device to skin.

18. A method of delivering an agent as claimed in claim 17 wherein the access means includes a self sealing port, the step of inserting the needle includes inserting the needle through the port, and after removing the needle the port self seals.

19. A method of delivering an agent as claimed in claim 18 wherein the protection means includes a shield positioned inside the reservoir and positioned opposite the port, the step of inserting the needle includes preventing the needle from damaging the diffusion membrane by the position of the shield.

20. A method of delivering an agent as claimed in claim 17 wherein the access means includes the backing layer being formed of an elastomeric material, the step of inserting the needle includes:

pinching the backing layer to form a puckered wrinkle;

inserting the needle through the puckered wrinkle; and after removing the needle, releasing the backing layer which seals upon release.

21. A method of delivering an agent as claimed in claim 20 wherein the protection means includes a shield positioned inside the reservoir and positioned opposite the access means, the step of inserting the needle includes preventing the needle from damaging the diffusion membrane by the position of the shield.

22. A method of delivering an agent as claimed in claim 17 wherein the reservoir is divided into a first portion and a second portion by a dividing membrane positioned intermediate the backing layer and the diffusion membrane, the step of filling the device includes filling the first portion of the reservoir with an agent and moving the agent from the first portion to the second portion through dividing membrane.

23. A method of delivering an agent as claimed in claim 22 wherein the dividing membrane includes an elastomeric material having a plurality of normally closed openings therethrough, and the step of moving the agent from the first portion to the second portion includes stretching the device thereby causing the normally closed openings open and applying pressure to the backing layer.

24. A method of delivering an agent as claimed in claim 17 wherein the step of adhering the device to skin includes adhering the device with the diffusion membrane adjacent the skin.

25. A method of delivering an agent as claimed in claim 17 wherein the step of adhering the device to skin includes adhering the device with the backing layer adjacent the skin.

26. A method of delivering an agent as claimed in claim 25 wherein the step of adhering the device to skin includes adhering the device to the skin of a septum of a nose allowing vapors to pass through the diffusion membrane into ambient air for inhalation.

27. A fillable dermal or transdermal device as claimed in claim 1 wherein the skin contact adhesive layer is carried by the diffusion layer and the backing layer is permeable to vapor such that vapor can exit or pass through the backing layer into ambient air.

28. A fillable dermal or transdermal device as claimed in claim 1 wherein the skin contact adhesive layer is carried by the backing layer for attachment to a septum of a nose and for allowing vapors to pass through the diffusion membrane into ambient air for inhalation.

* * * * *

UNITED STATES PATENT AND TRADEMARK OFFICE
CERTIFICATE OF CORRECTION

PATENT NO. : 5,827,530
DATED : 27 OCTOBER 1998
INVENTOR(S) : FRED DEWITT REED, JR.

It is certified that error appears in the above-indentified patent and that said Letters Patent is hereby corrected as shown below:

REPLACE "tillable" in column 3, line 57 with --fillable--.

REPLACE "tillable" in column 4, line 6 with --fillable--.

REPLACE "tillable" in column 5, line 63 with --fillable--.

REPLACE "tillable" in column 6, line 4 with --fillable--.

REPLACE "tillable" in column 6, line 8 with --fillable--.

Signed and Sealed this

Twenty-fourth Day of August, 1999

Attest:

Q. TODD DICKINSON

Attesting Officer

Acting Commissioner of Patents and Trademarks